(12) United States Patent
Borsholm et al.

(10) Patent No.: US 10,282,826 B2
(45) Date of Patent: May 7, 2019

(54) DESPECKLING METHOD FOR RADIOGRAPHIC IMAGES

(71) Applicant: Carestream Health, Inc., Rochester, NY (US)

(72) Inventors: Atle Borsholm, Louisville, CO (US); James L. Pendleton, Erie, CO (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 15/619,636

(22) Filed: Jun. 12, 2017

(65) Prior Publication Data

US 2018/0101937 A1   Apr. 12, 2018

Related U.S. Application Data

(60) Provisional application No. 62/406,122, filed on Oct. 10, 2016.

(51) Int. Cl.
*G06K 9/00*   (2006.01)
*G06T 5/00*   (2006.01)
*G01N 23/04*   (2018.01)

(52) U.S. Cl.
CPC .......... *G06T 5/005* (2013.01); *G01N 23/04* (2013.01); *G06T 5/002* (2013.01); *G01N 2223/401* (2013.01); *G06T 2207/10116* (2013.01)

(58) Field of Classification Search
CPC combination set(s) only.
See application file for complete search history.

(56) References Cited

U.S. PATENT DOCUMENTS

| | | | |
|---|---|---|---|
| 7,068,854 B1 * | 6/2006 | Aufrichtig | G06T 3/4015 250/208.1 |
| 7,218,425 B2 | 5/2007 | Saida et al. | |
| 8,314,844 B2 | 11/2012 | Tashiro et al. | |
| 8,351,736 B2 | 1/2013 | Demandolx et al. | |
| 8,908,954 B2 * | 12/2014 | Svenonius | G06T 5/002 250/370.11 |
| 2007/0065009 A1 * | 3/2007 | Ni | G01S 7/52034 382/173 |

* cited by examiner

*Primary Examiner* — Alex Kok S Liew

(57) ABSTRACT

A method includes acquiring a radiographic image and processing the acquired image to obtain a gradient image. The method then includes generating, from the gradient image, an initial set of pixels exhibiting speckle and removing one or more pixels from the initial set of pixels according to features indicative of image content, forming a mapping of pixels for replacement from the remaining set of pixels. A replacement pixel value is calculated for one or more pixels in the mapping and pixel values from the acquired radiographic image replaced according to the calculated replacement pixel value to form a corrected image. The corrected image can be displayed.

13 Claims, 13 Drawing Sheets

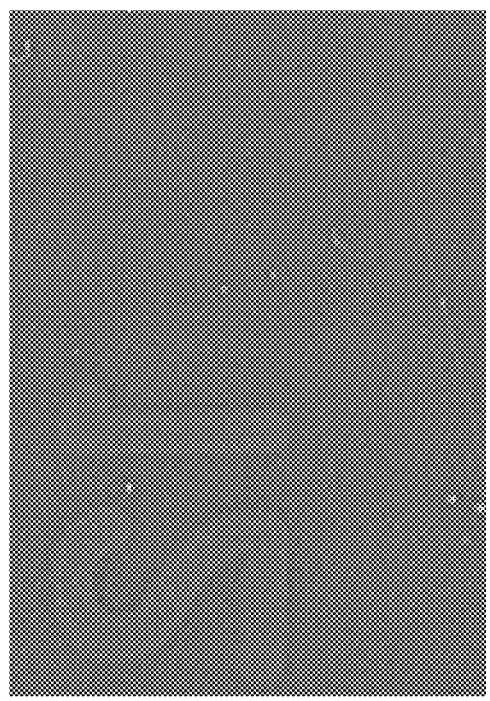
FIG. 4A
FIG. 4B

DESPECKLING METHOD FOR RADIOGRAPHIC IMAGES

CROSS REFERENCE TO RELATED APPLICATIONS

This application claims the benefit of U.S. Provisional application U.S. Ser. No. 62/406,122, provisionally filed on Oct. 10, 2016, entitled "DESPECKLING METHOD FOR RADIOGRAPHIC IMAGES", in the names of Borsholm et. al., which is incorporated herein by reference in its entirety.

FIELD OF THE INVENTION

The present disclosure relates generally to correction of image artifacts and more particularly to correcting speckle artifacts in radiographic images.

BACKGROUND OF THE INVENTION

Radiographic imaging is a familiar tool not only for medical and dental diagnostics, but also for security identification and non-destructive test (NDT) applications. In radiographic imaging a detector, placed behind the subject with respect to the radiation source, responds to directed radiation by forming an image that is representative of the relative absorption of incident X-rays by the subject. Detector types for X-ray imaging range from digital radiography (DR) devices that generate electronic image data directly, to computed radiography (CR) apparatus that employ a re-usable phosphor sheet or plate that is scanned following exposure, and to film X-ray systems that can be scanned and digitized to provide digital image data.

Speckle artifacts can occur in the X-ray image, particularly in industrial and test environments, due to various types of particulate in the imaging path. This can include dust or dirt, metal filings, or other contaminants on the X-ray plate itself or on or near other components in the imaging chain. Unless speckle is suppressed, the resulting displayed image can be difficult to interpret, compromising the usefulness of the radiographic image as a diagnostic testing tool.

Conventional approaches to the problem of correcting image speckle have not been satisfactory, for various reasons. The problem is complex, since speckle can occur anywhere in the image, over both highly absorptive and non-absorptive portions of the subject. This means that data values for speckle can vary within the same image, depending on location, and frustrates more straightforward approaches, such as applying global thresholding to identify and isolate speckle, for example. Statistical methods that detect dust or other particulate can be of some value; however, such methods inherently require multiple image captures from the same equipment and taken in the same environment, which may not be possible for some applications and can be costly and time-consuming, generating considerable data that is not used directly for imaging.

It is preferred that the method for threshold correction should not compromise the image content. Thus, there is a need for a speckle suppression method that selectively identifies speckle in each image and compensates for speckle artifacts without distorting the data content.

SUMMARY OF THE INVENTION

An object of the present disclosure is to advance the art of image processing for radiographic images. Advantageously, certain embodiments described herein address the problem of speckle suppression for a radiographic image. The disclosure offers methods for speckle artifacts detection and correction that preserve the useful image content.

While particularly useful for speckle suppression in NDT and other industrial use environments, embodiments of the present disclosure can be used in other applications, including medical and dental imaging, for example. Speckle suppression as described herein can be applied to X-ray image content from CR, DR, or scanned film sources. Multiple images are not required; the method of the present disclosure can be used on any single radiographic image.

These objects are given only by way of illustrative example, and such objects may be exemplary of one or more embodiments of the disclosure. Other desirable objectives and advantages inherently achieved by the disclosed embodiments may occur or become apparent to those skilled in the art. The invention is defined by the appended claims.

According to one aspect of the disclosure, there is provided a method comprising: acquiring a radiographic image; processing the acquired image to obtain a gradient image; generating, from the gradient image, an initial set of pixels exhibiting speckle; removing one or more pixels from the initial set of pixels according to features indicative of image content and forming a mapping of pixels for replacement from the remaining set of pixels; calculating a replacement pixel value for one or more pixels in the mapping; replacing one or more pixel values from the acquired radiographic image according to the calculated replacement pixels value to form a corrected image; and displaying the corrected image.

BRIEF DESCRIPTION OF THE DRAWINGS

The foregoing and other objects, features, and advantages of the methods of the present disclosure will be apparent from the following more particular description of the embodiments, as illustrated in the accompanying drawings.

The elements of the drawings are not necessarily to scale relative to each other.

FIG. 4A shows a portion of an original radiographic image with a number of speckle artifacts.

FIG. 4B shows the corresponding convolved or gradient-filtered image obtained for the region of FIG. 4A using difference of Gaussian kernels processing.

DETAILED DESCRIPTION OF THE INVENTION

Figure 1:
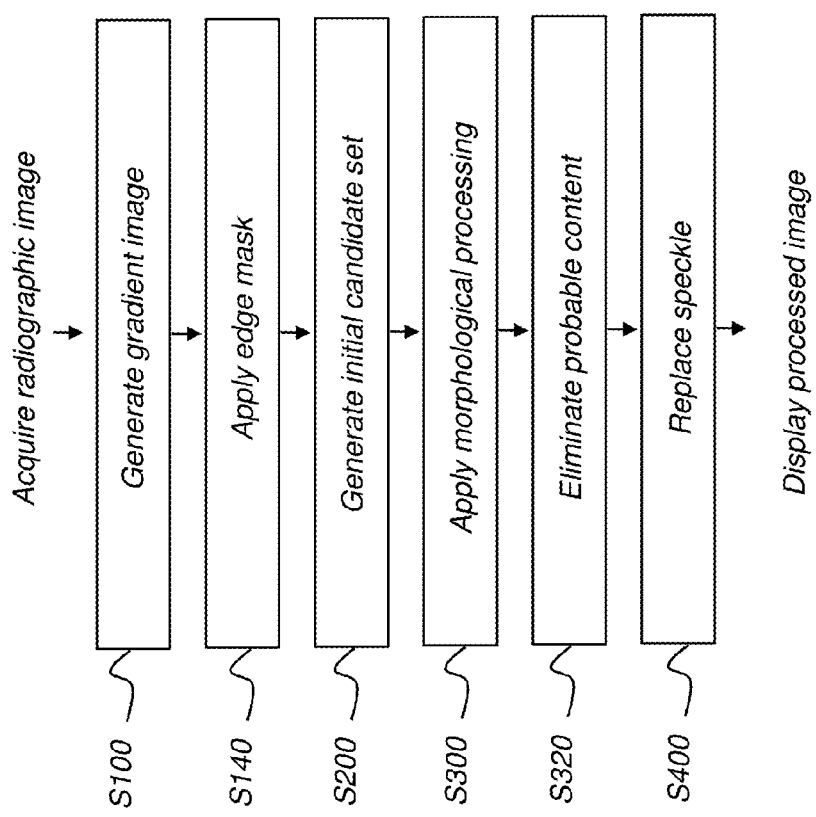
FIG. 1 is a logic flow diagram that shows a generalized sequence for speckle detection and suppression according to an embodiment of the present disclosure.

The following is a detailed description of the preferred embodiments of the disclosure, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the terms "viewer", "operator", and "user" are considered to be equivalent and refer to the viewing practitioner or other person who views and manipulates an X-ray image on a display monitor.

As noted previously, dust and particulate in the imaging chain can result in speckle within the image; thus the two terms can be used interchangeably, depending on the context. In the present disclosure, the term "dust", when describing unwanted image content that is chiefly due to particulate in the imaging environment, can be understood equivalently with "speckle" or "speckle artifact" unless otherwise noted.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members. For a set S, a subset may comprise the complete set S. A "proper subset" of set S, however, is strictly contained in set S and excludes at least one member of set S. A "partition of a set" is a grouping of the set's elements into non-empty subsets so that every element is included in one and only one of the subsets. Two sets are "disjoint" when they have no element in common.

The terms "image" and "image data" can be used interchangeably in the context of the present disclosure. An image that is captured by an imaging apparatus is processed, displayed, transmitted, and stored as image data.

Reference is hereby made to U.S. Pat. No. 8,351,736 (Demandolx) entitled "Automatic Dust Removal in Digital Images"; U.S. Pat. No. 8,314,844 (Tashiro) entitled "Image Pickup Apparatus, Method and Computer-Readable Storage Medium for Processing an Image Based on User Manipulation on a Display Surface"; and U.S. Pat. No. 7,218,425 (Saida) entitled "Dust and/or dirt detection in image reading apparatus having read-while-feed function". All of which are incorporated herein by reference in their entirety.

Applicants have recognized that effective speckle detection requires techniques that work over the full range of image data values obtained from the radiographic image acquisition system. In order to address speckle suppression for any type of radiographic system, the method described herein operates on units of pixels rather than using actual feature dimensions. It is noted that this approach can be used for image processing at any arbitrary resolution, provided there is appropriate scaling of image processing and calculations.

The logic flow diagram of FIG. 1 shows a generalized sequence for speckle detection and suppression according to an embodiment of the present disclosure. In a gradient sensing step S100, an acquired radiographic image is processed, generating a filtered image that accentuates image speckle artifacts in the image according to a gradient characteristic. An optional edge mask application step S140 masks one or more of the four edges of the image to a certain width or height in order to remove peripheral pixels from speckle processing, as possible sources of error. An initial candidate generation step S200 then processes the gradient-filtered image for detection of an initial candidate set of speckle regions. A morphological processing step S300 provides tools that help to distinguish true features of the imaged subject from speckle in the image content. A content elimination step S320 removes ineligible candidates from the initial candidate set to form a speckle subset of identified regions for correction. A replacement step S400 then replaces members of the speckle subset with image content using known tools for in-painting.

Generating a Gradient-Filtered Image

Gradient sensing step S100 of FIG. 1 processes the acquired radiographic image to identify candidate speckle areas and their corresponding pixels based on gradient characteristics. According to an embodiment of the present disclosure, this processing uses a difference of two Gaussian kernels of different pixel-by-pixel ("pixel×pixel") dimensions, with kernel sizes variable and relating to the relative size of dust and particulate and corresponding speckle and to the imaging resolution of the detector. In terms of pixel×pixel dimensions for one detector type, for example, the two kernels can measure 5×5 and 1×1; 7×7 and 3×3; or 9×9 and 5×5 pixels according to an embodiment. Other sizes and kernel shapes could alternately be used, taking into consideration the dimensional factors noted above. As detector pixel resolution increases, kernel dimensions would be adjusted upwards accordingly.

Figure 2:
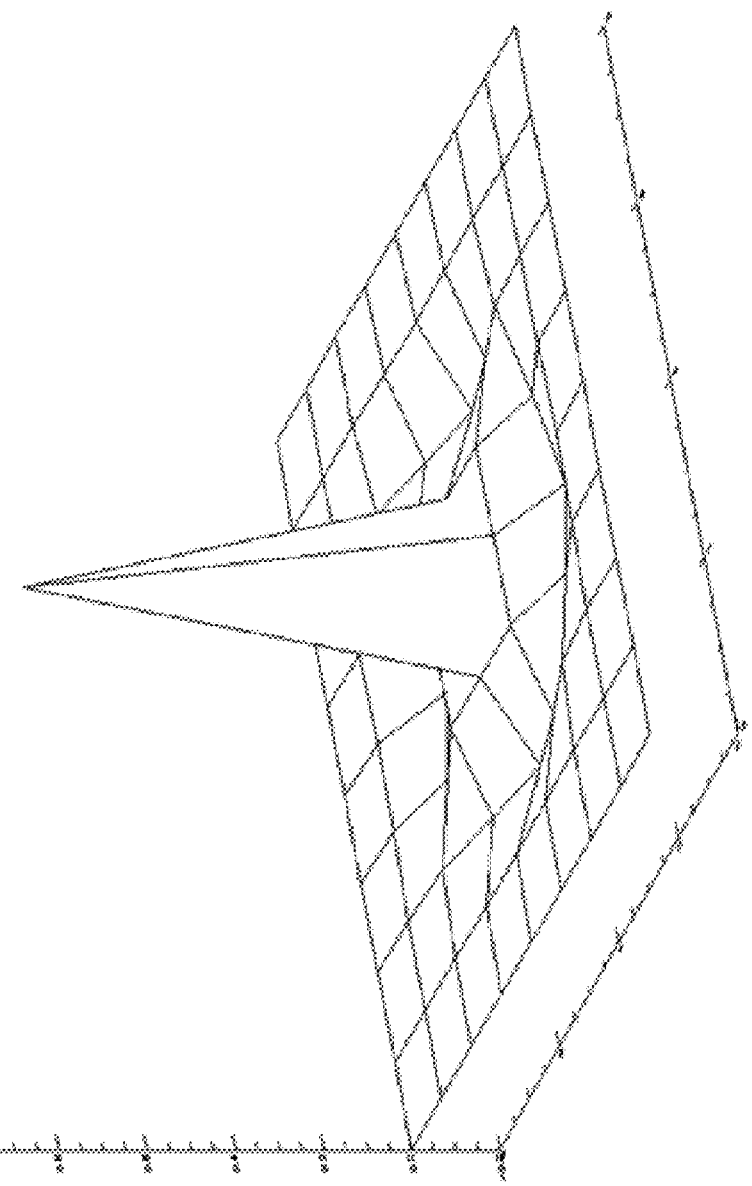
FIG. 2 shows a graphic representing a combined convolutional kernel that applies difference of gradient filtering to an image.

The 3D graph of FIG. 2 shows a graphic representation of a combined convolution kernel that applies difference-of-gradient filtering to an image. Units shown are in pixels. Here, the example kernel results in a subtraction of neighboring pixels from the central pixel. The enlarged plan view of FIG. 3 shows a plan view of a 9×9 kernel of this type in image form.

Figure 3:
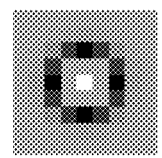
FIG. 3 shows, in plan view, a kernel that applies difference of gradient filtering in image form.

When the combined kernel of FIGS. 2 and 3 is convolved with the input image's raw data, it produces an output that accentuates or highlights areas of steep gradient, where pixels exhibit relatively rapid change in values, having values that are pronouncedly different from their nearest neighbors. Significantly, the output image from this processing, termed a gradient or gradient-filtered image because it shows and accentuates gradient features, is in units derivative of the original values but accentuating aspects of the relative change of data values of the original image data. By way of example, FIG. 4A shows a portion of an original radiographic image 20, with a number of speckle artifacts. FIG. 4B shows the corresponding convolved, gradient, or gradient-filtered image 24 obtained for this region using difference of Gaussian kernels processing. Speckle content from the original image is retained at relatively high contrast, but image content itself is muted or de-emphasized.

It can be appreciated that the filtering method used can alternately be adapted for pixels of various sizes or for imaging areas that use larger pixels.

Generating a Set of Initial Candidates

Initial candidate generation step S200 in FIG. 1 then processes the convolved image shown in the example of FIG. 4B in order to identify possible speckle artifacts or dust from the gradient-processed data. As the process of FIG. 1 showed, membership of this set is then modified in subsequent processing to eliminate true features of the imaged subject from consideration as speckle.

An embodiment of the present invention identifies initial speckle candidates using a local analysis of the convolved image of FIG. 4B. To do this, processing uses a tiled approach, wherein the convolved gradient image 24 is analyzed as a tiling of small areas, each tile bounding a partial portion of the image for localized analysis. Each pixel of image 24 is analyzed for speckle, one small tile at a time. Tiles can be square or rectangular subsections of the image and can overlap, allowing the same area to be analyzed multiple times. Tile dimensions and amount of overlap from one tile position to the next can be adjustable in order to improve processing results. The tile-by-tile processing can proceed methodically through the image, such as by moving incrementally from left to right and top to bottom, for example.

Figure 5B:
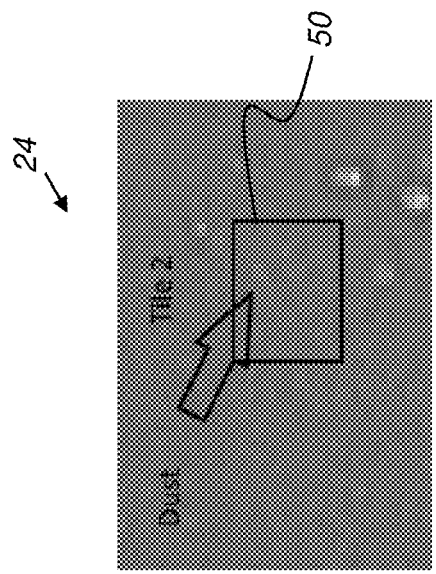
FIGS. 5A and 5B show an enlarged view of different tiles used at different positions over adjacent portions of the convolved image.
Figure 5A:
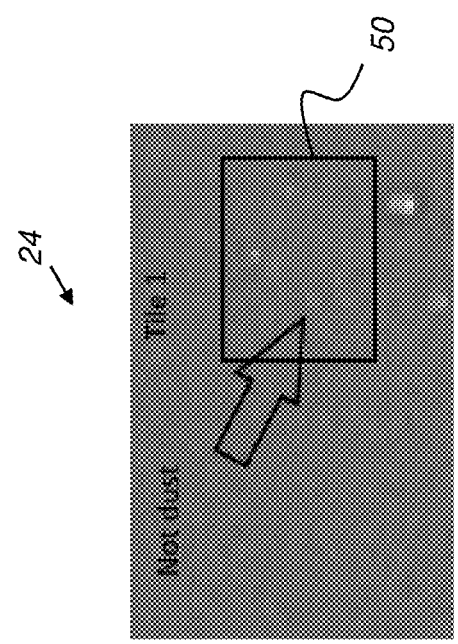

FIGS. 5A and 5B show an enlarged view of different tiles 50 used at different positions over adjacent portions of image 24. Using overlap as part of this processing, each pixel in the image can be considered for speckle or dust-like characteristics in one or more tiles, depending on the overlap parameter. In some cases, a single pixel or grouping of pixels may be statistically "not dust" (that is, not a speckle candidate) when it is on the left side of one tile, but identified as "dust" when an overlapping tile calculation positions the pixel(s) in a different population distribution, for example on the right hand side of a subsequent tile.

It can be appreciated that various rules can be applied for positively identifying a pixel that indicates a speckle candidate, depending on the analysis results from tiling. For example, once a pixel is identified as part of a speckle artifact, it may be admitted to the candidate set and its removal from the set not permitted until later steps in processing. Or, it may be required that a particular anomalous pixel be determined to be part of a speckle artifact when identified as a candidate from analysis in at least two tiles. Other weighting or voting schemes can be applied for implementing candidate set membership decisions for a pixel.

Figure 6:
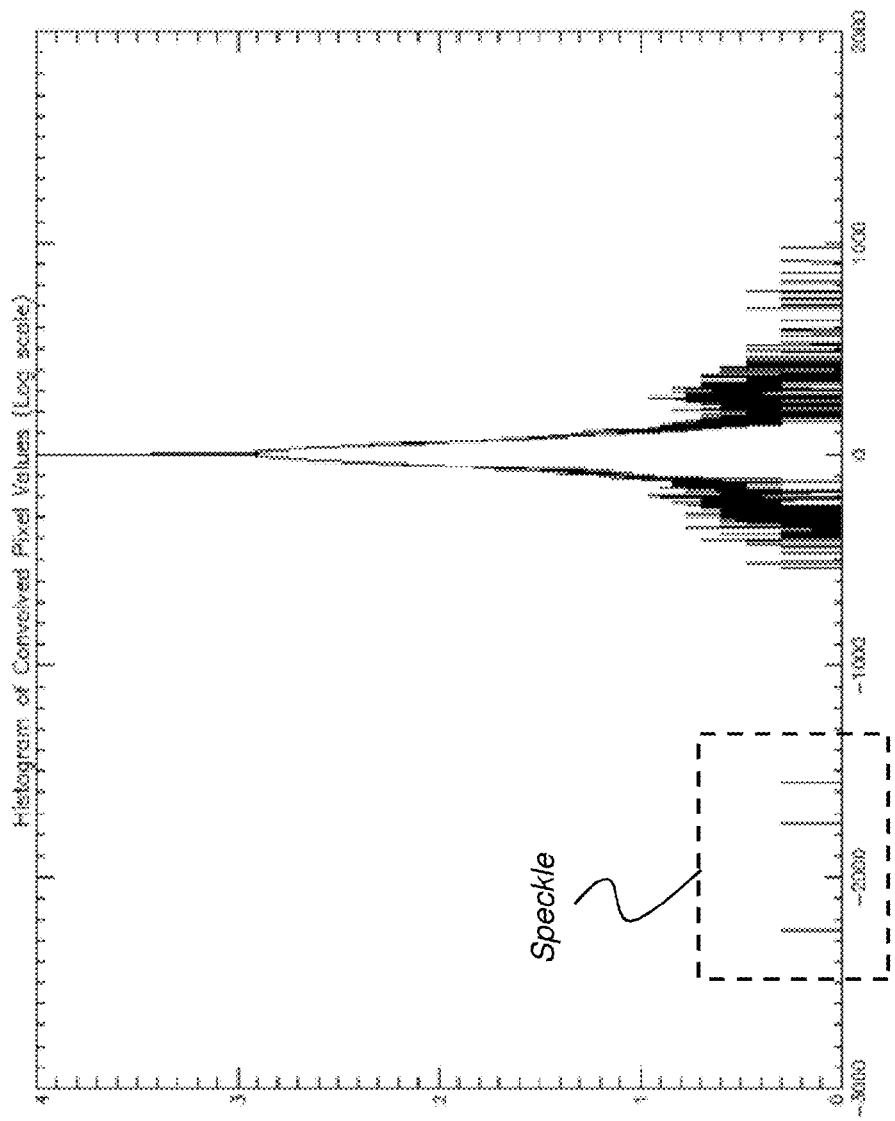
FIG. 6 shows a histogram for a single tile.

A histogram can be generated for each tile, as shown in FIG. 6. In the particular example shown, the bulk of true image content is roughly centered about value 0 in the abscissa. The three peaks at the left that are bounded by a dashed box indicate pixels that are speckle candidates, likely representative of dust or other particulate. Their data values indicate relative intensity, such as brightness in typical X-ray display, in the displayed radiation image due to high absorption.

A number of different tests and criteria could be used in order to determine whether or not a particular image feature in the gradient image represents a speckle artifact. According to an embodiment of the present disclosure, thresholding could be used to make this distinction, so that values less than some numeric threshold can be considered as lying within the threshold for membership in the initial candidate set. Population statistics can alternately be used, so that pixels with values below a certain population threshold in the histogram for a tile, regardless of the minimum value in the population, are considered as candidates, for example.

Figure 7:
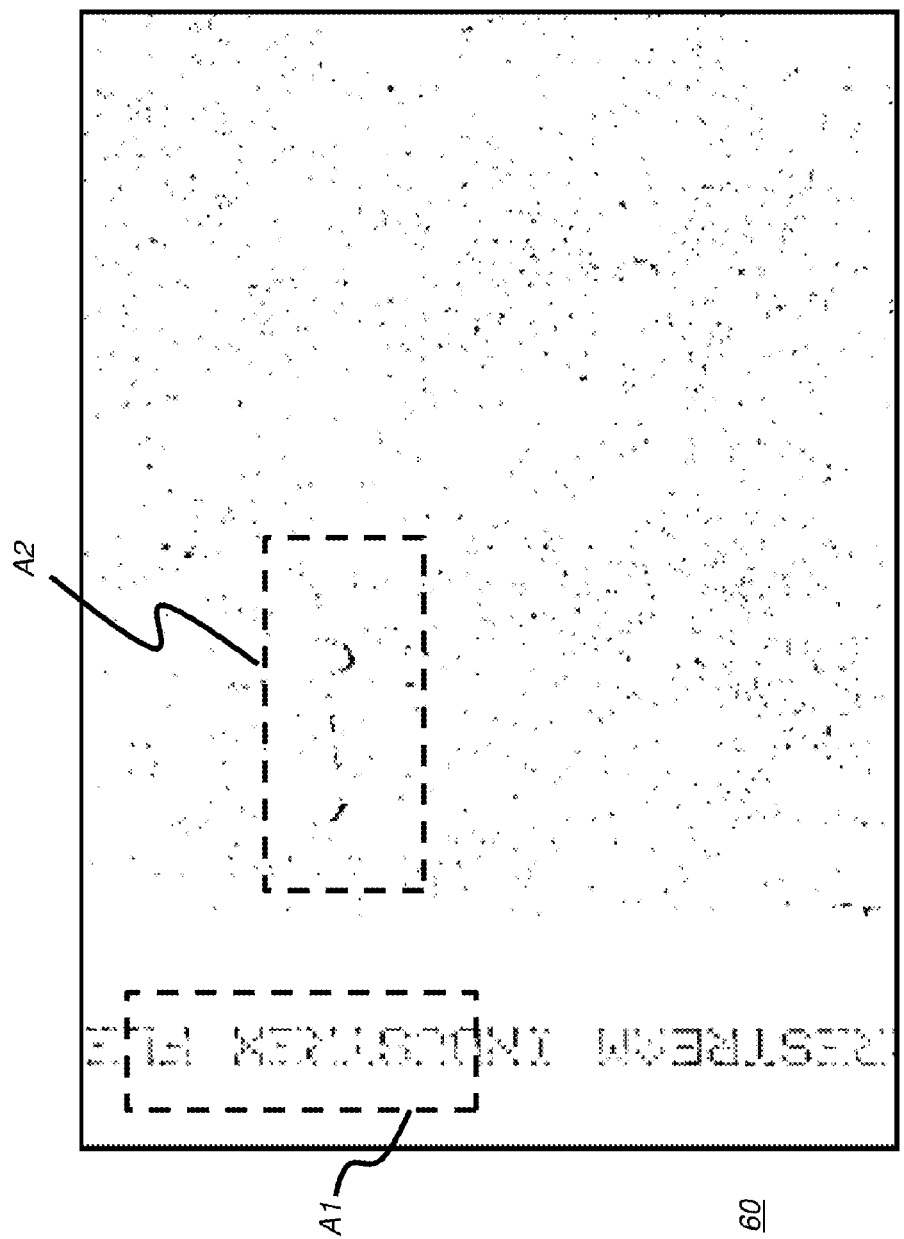
FIG. 7 is a plan view that shows the resulting binary mask from an image having lettering.

According to an embodiment, the initial candidate set formed using analysis of the gradient image is used to generate a binary mask or other type of mapping that differentiates candidate speckle pixels from pixels indicative of true image content. The plan view of FIG. 7 shows a resulting binary mask 60 from an image having lettering. Black dots on the mask 60 indicate pixels in the initial candidate set. As can readily be seen, some pixels in the candidate set clearly relate to actual image content and need to be removed from the initial candidate set. An area A1, for example, includes text that is part of the image content, such as default text provided on the edge of a CR medium or film. An area A2 includes a feature in the corresponding X-ray image that is more difficult to distinguish, but appears to be true image content rather than speckle.

Morphological Processing

Morphological processing uses one or more utilities that help to distinguish between speckle artifacts and true features of the image content. This provides help for removing masked pixels that are associated with true image content from the initial candidate set. As shown in FIG. 1, the results of morphological processing step S300 then go to a content elimination step S320 that refines the initial candidate set to obtain a set of speckle-related pixels that are likely to be the result of dust or other particulate and are suitable for replacement.

Known morphological operators can be used for step S300, including dilation and erosion, for example. One function of morphological processing is to check for connectedness of pixels that have otherwise exhibited characteristics common to speckle. Pixel connectedness in an image is a concept well understood by those skilled in the image processing arts. Pixel connectedness metrics relate to image characteristics such as number of pixels having similar characteristics and their relative spatial arrangement, such as for pixels forming or along lines or edges, for example. Where pixels are grouped and appear to be connected as part of the same object or body type, various checks can be made to determine whether these pixels indicate larger speckle artifacts or true features. Areas A1 and A2 in FIG. 7 show examples in which some of the pixels identified as speckle in the initial candidate set generated in step S200 are not speckle, but actually relate to true image features.

For step S300 of FIG. 1, a standard set of dilation and erosion convolution operators can be applied to the binary mask generated from step S200. Detection routines can apply probabilistic approaches and metrics. The structure of connected pixels can be one characteristic used to distinguish true content from speckle. For example, the roundness and size of any region can be checked in order to make this determination. In practice, it has been found that most speckle artifacts caused by dust are generally round and have diameters within a given range. Asymmetric and oversized features can thus be considered less likely speckle artifacts and eliminated from the candidate set. The mask can be reset to 0 (ignored) at each of the pixel locations if a clump of pixels that might otherwise represent a dust feature is too large or too small.

Neighboring pixels can be examined in order to determine whether they indicate a continuous line or curve extending in any direction, or other feature of the imaged subject. Some variability can be provided for controlling the relative aggressiveness of this processing, including designating the number of passes over the mask and other parameters.

Figure 8:
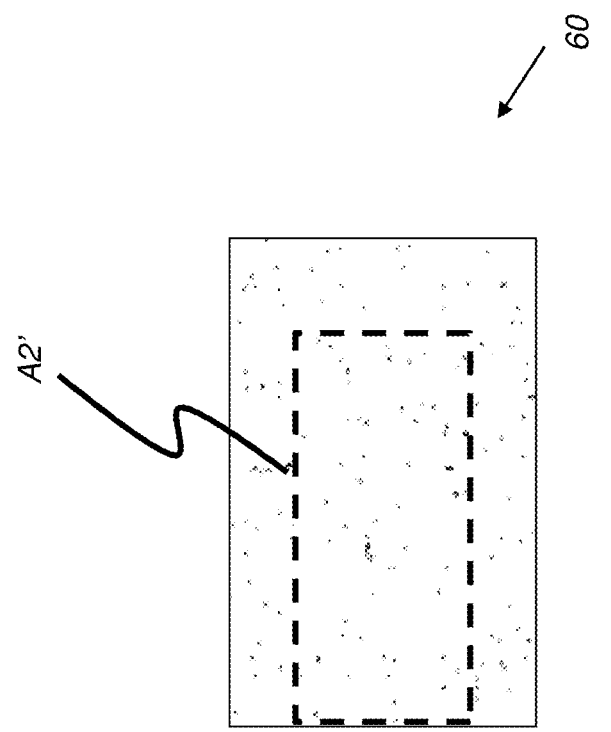
FIG. 8 shows an area of the mask of FIG. 7 with corrected speckle pixels.

FIG. 8 shows an area A2' corresponding to area A2 in the mask 60 of FIG. 7 and having corrected speckle pixels identified. Connected pixels associated with image content have been removed from the mask.

Following morphological processing step S300 and content elimination step S320, the initial candidate set has been refined and pared down to a subset of more likely speckle artifact pixels.

Correcting Speckle

Pixel replacement step S400 in the FIG. 1 sequence operates to suppress speckle artifacts by computing and applying a new value to each pixel defined in the binary mask. Replacement step S400 applies one or more digital "in-painting" approaches that compute replacement values for a pixel using values from neighboring content. According to an embodiment, for a pixel that has been determined to be speckle, a weighted average of neighboring pixels that have been determined to be true image content can be computed and used for pixel replacement. Other interpolation methods can be used. Alternately, a median filter replacement value can be used. Still other alternate in-painting approaches for pixel replacement can include recursive annealing across a 2-D dimensional surface fit, for example.

In an optional step as part of replacement step S400, the mask data can be further processed, such as using recursive dilation, for example. A parameter can be set to define the number of times the mask image for dust and other particulates is dilated, using the same kernel that was used to group pixels. Blurring the mask has the effect of attaching neighboring pixels to the speckle artifact pixels that were not originally counted as dust according to their characteristics and image statistics. This optional step can be useful if it is found, for example, that dust "centers" are successfully removed but margins are not, causing a "halo" effect where the speckle is partially replaced. Balanced application of blurring is needed, since this processing, if applied too aggressively, can also have the potential effect of causing valid pixels to be replaced.

Figure 9:
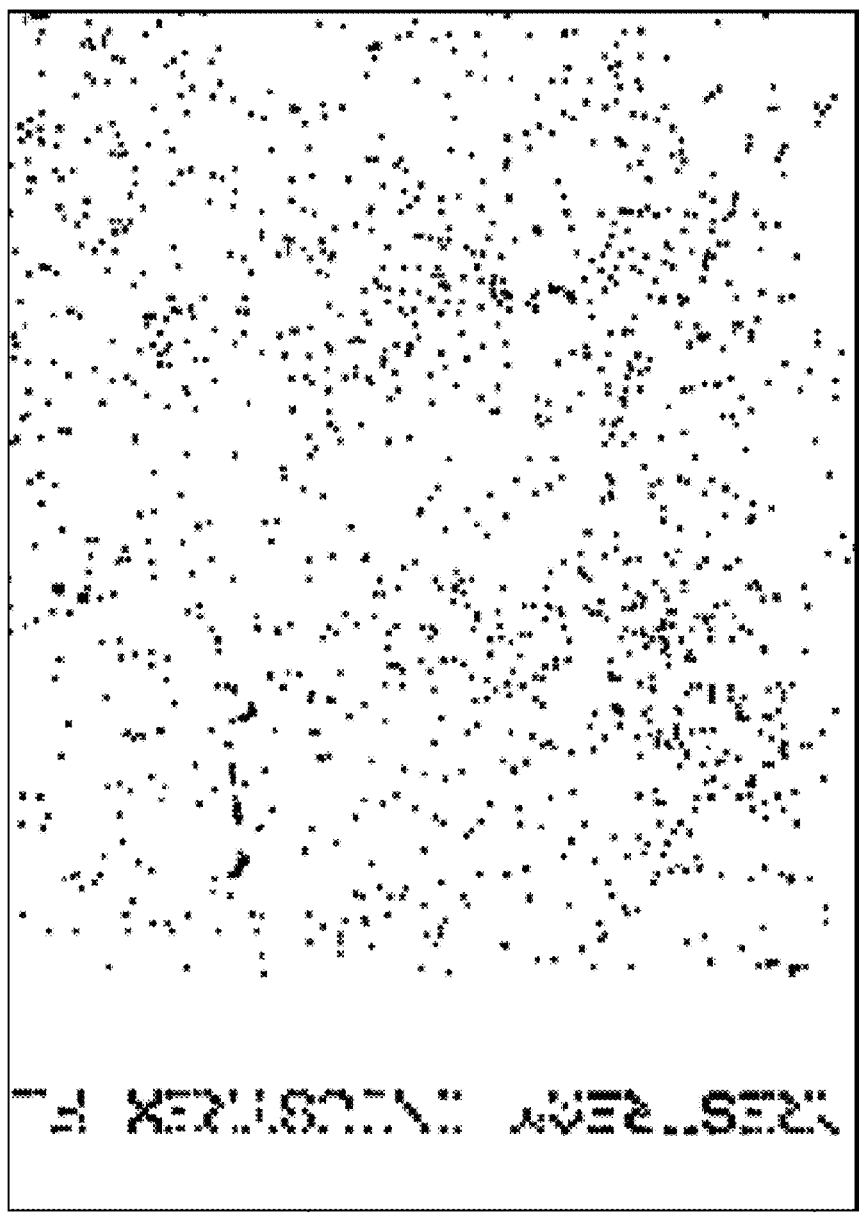
FIG. 9 shows a blurred mask.

In the example shown in FIG. 9, binary mask 60 has been blurred two times.

Figure 10:
FIG. 10 is a plan view of a portion of an original image having speckle artifacts.
Figure 12:
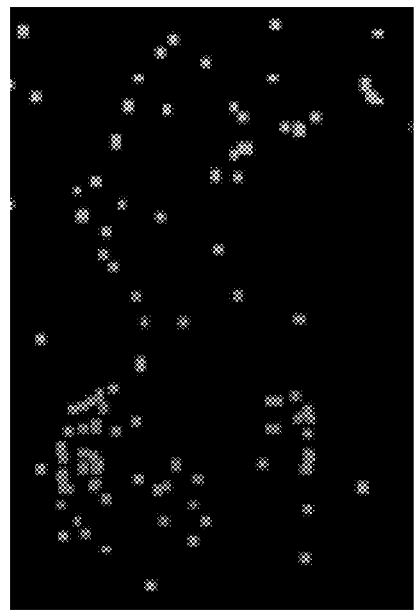
FIG. 12 is a plan view of the corresponding set of replacement pixels for the pixel positions shown in FIG. 11.
Figure 11:
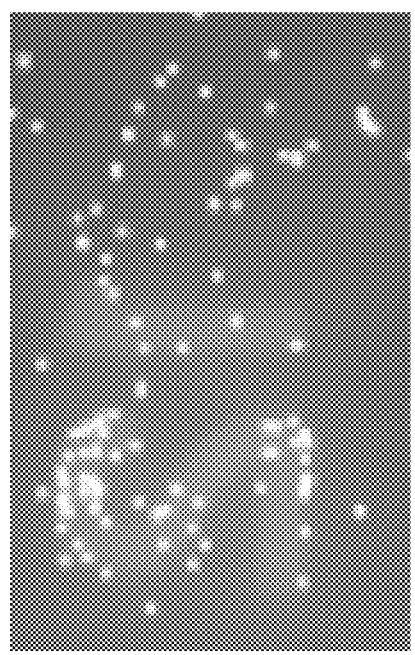
FIG. 11 is a plan view of the pixel mask showing positions of speckle artifacts.
Figure 13:
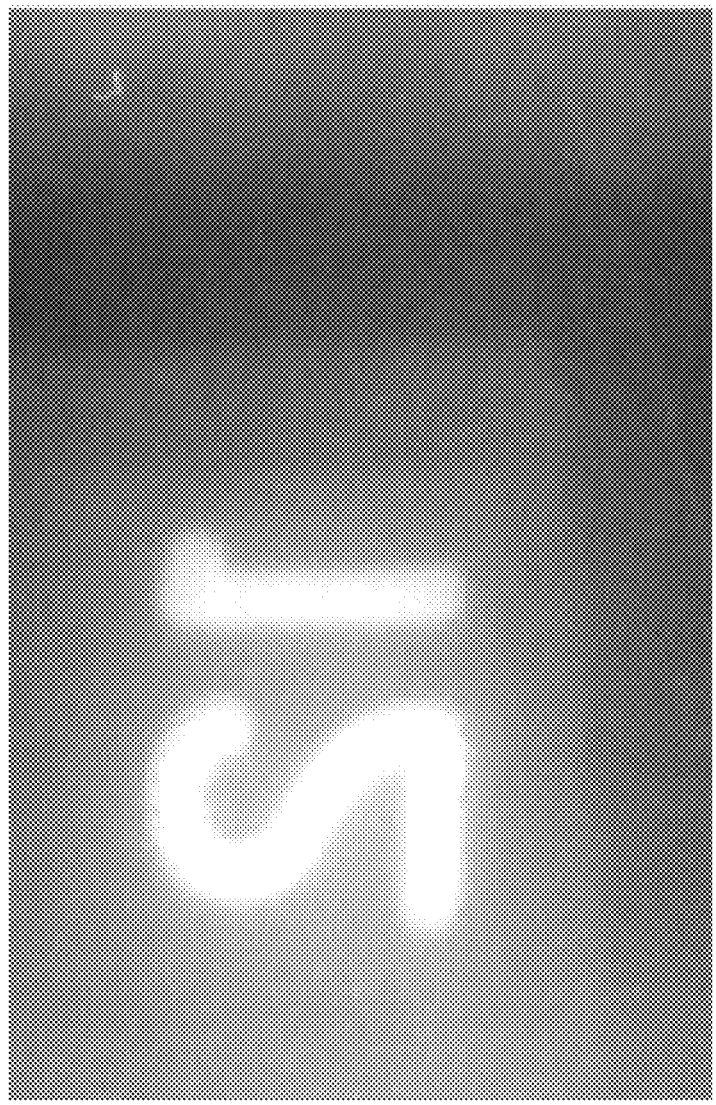
FIG. 13 is a plan view showing the speckle-corrected image.

The sequence of FIGS. 10-13 shows an example using the processing shown in FIG. 1 and described herein. FIG. 10 is a plan view of a portion of an original image having speckle artifacts. FIG. 11 is a plan view of the pixel mask generated using the gradient image and associated processing as described previously, showing positions of speckle artifacts. FIG. 12 is a plan view of the corresponding set of replacement pixels for the pixel positions for the mask shown in FIG. 11. FIG. 13 is a plan view showing the speckle-corrected image.

The original pixel values from the input image remain intact in areas where no dust is present and the pixels representative of dust particles and appearing as speckle are replaced with the estimated values from the final convolution. This is the final "despeckled" filter operation. The final display values can be stretched using standard display techniques, such as linear, logarithmic, or S-curve scaling with window/level thresholds applied.

Selectable Options

According to an embodiment of the present disclosure, there are a number of selectable parameters for speckle handling logic for the process of FIG. 1 that can be adjusted to improve de-speckling performance in individual applications. Exemplary values that can be adjusted can include the following:

(i) Width, in pixels, of the Gaussian kernel to be convolved with the raw image data to produce a gradient image for further analysis. This value typically is greater than or equal to 5 and an odd number. Values obtained using the smaller kernel can then be subtracted from those obtained using the larger kernel in order to compute the gradient. The appropriate Gaussian kernel size can depend on the relative size of what appears as speckle due to dust or other particulate in a given image.

(ii) The width, in pixels, of the border around the outer perimeter of the raw data that should not be included in the dust identification and speckle processing, in order to avoid edge effects.

(iii) The width and height dimensions of a processing tile of the convolved image, in pixels. A processing tile is a square or rectangular subset of the image within which population statistics are calculated individually. Each tile can be square; however, if the width of the image does not accommodate an exact subdivision into tiles based on the tile size, the tiles at the right and top of the image can be rectangular and have fewer pixels. The tile size should be selected based on the typical larger-scale variation of the "non-dust" image content.

(iv) The width of the overlap between tiles, in pixels. For example, if the tile size is 128 and the overlap is 128, the second tile in sequence can contain 64 pixels from the first tile and 64 from the next tile.

(v) The allowable percentage of the population of pixels within a given tile that may be considered "dust" candidates, based on the population statistics of that tile alone. Values can be floating point, for example a value of 0.5 is one half of one percent. For a tile of 128×128 pixels, one-half percent would capture, at most, 81 pixels as candidates for being dust or other particulate.

(vi) Number of iterations of dilate and erode to iterate in order to "re-connect" clumps of pixels that are in close proximity, in order to exclude extended features from consideration as dust.

(vii) Erosion and dilation kernel size to be used when reconnecting "clumps" of pixels in close proximity.

(viii) A minimum number of pixels in a clump to be considered dust.

(ix) A maximum number of pixels in a clump to be considered dust.

(x) Maximum length of a region in either the X or Y dimension.

(xi) A flag with allowed values of 0 or 1 that indicates whether the dimensions of each speckle candidate should be checked for approximate equality in X and Y size, which can serve as a proxy for locating more-or-less circular objects.

(xii) A value indicating the number of times the mask can be dilated to attempt to include "margin" pixels along the edges of dust before pixel replacement.

GUI

Figure 14:
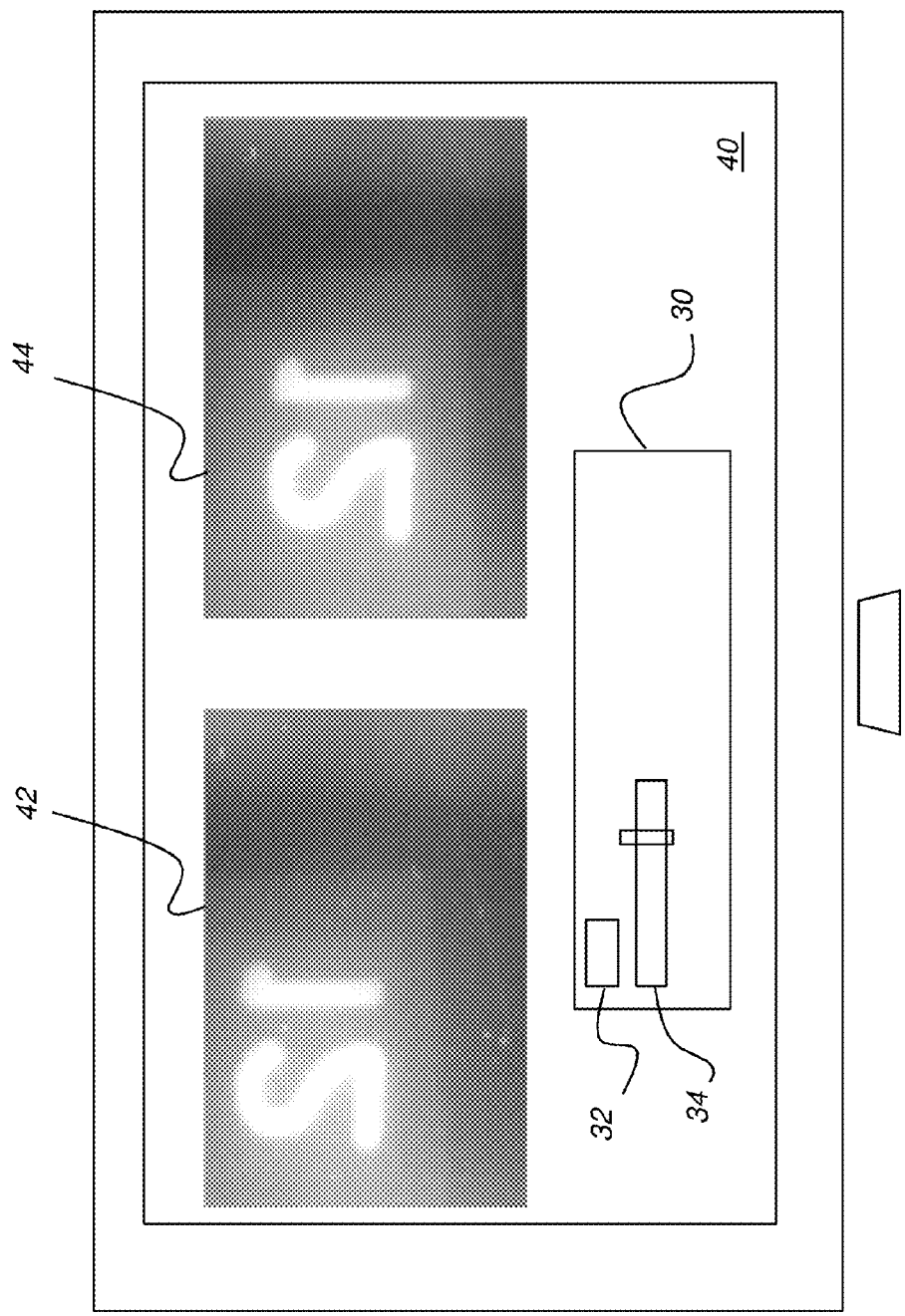
FIG. 14 shows an exemplary arrangement for a user interface display.

According to an embodiment of the present disclosure, an operator interface or graphical user interface (GUI) is provided for display of speckle processing control options and results. FIG. 14 shows, side-by-side for comparison, a display 40 that shows an original radiographic image 42, as acquired, and a processed image 44. A control panel 30 includes various types of controls for parameter settings, such as those previously described, using text entry or tools such as a toggle 32 or pushbutton or a slide bar 34, for example. This GUI gives the operator the option to adjust speckle suppression software for more or less aggressive behavior for handling an individual image. Controls in control panel 30 can be touch-screen controls, for example, or can accept manually entered commands or values. Optionally, controls can be provided on separate hardware. According to an embodiment of the present disclosure, viewer adjustment of controls causes automated recomputation and reprocessing, and refreshed display of processed image 44 showing the adjustment.

Figure 15:
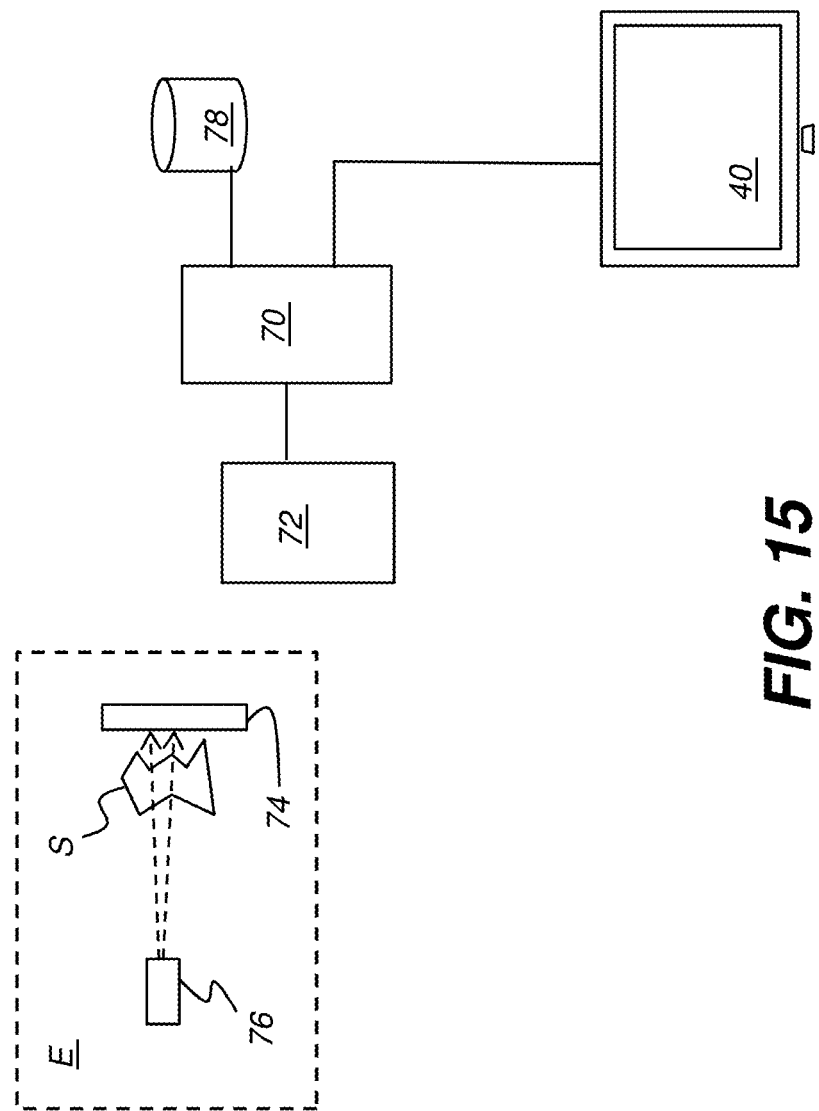
FIG. 15 is a schematic diagram that shows a generalized imaging chain for radiographic imaging and display according to an embodiment of the present disclosure for using a CR imaging apparatus.

Speckle processing and suppression as described herein can be applied for a radiographic image from any of a number of types of imaging apparatus, including CR, DR, or scanned film apparatus. The schematic diagram of FIG. 15 shows a generalized imaging chain for radiographic imaging and display according to an embodiment of the present disclosure for using a CR imaging apparatus. Within an imaging environment E for imaging a subject S, an X-ray source 76 directs radiation through subject S and toward a detector 74 such as a CR cassette, for example. A scanner 72 is energizable to read the exposed CR plate and digitize the image for a processor 70 that is in signal communication with scanner 72. Processor 70 includes the control logic instructions for display of the processed image content and storage in a memory 78. The original image, as acquired, can be stored, along with processed versions of the image that have speckle suppression. Similar apparatus would be used for film apparatus, with scanner 72 configured to scan and digitize the developed film image. Scanner 72 would not be needed for DR apparatus; the DR image can be provided directly from the detector 74.

Consistent with one embodiment, the present invention utilizes a computer program with stored instructions that control system functions for image acquisition and image data processing for image data that is stored and accessed from a scanner or from an electronic memory. As can be appreciated by those skilled in the image processing arts, a computer program of an embodiment of the present invention can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present invention, including an arrangement of networked processors or a mobile device, such as a smartphone or tablet, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for correcting image speckle in a radiographic image, comprising:
   processing the radiographic image to obtain a gradient image;
   generating, from the gradient image, an initial set of pixels exhibiting speckle, wherein generating the initial set of pixels exhibiting speckle comprises evaluating image data values from the gradient image using a plurality of tiles, wherein each tile defines a partial portion of the image;

removing one or more pixels from the initial set of pixels according to at least one feature indicative of image content and forming a mapping of pixels for replacement from the remaining set of pixels;

calculating a replacement pixel value for one or more pixels in the mapping;

replacing one or more pixel values from the acquired radiographic image according to the calculated replacement pixel value to form a corrected image; and displaying, storing, or transmitting the corrected image.

2. The method of claim 1 further comprising acquiring the radiographic image using a digital radiography or a computed radiography apparatus.

3. The method of claim 1 further comprising acquiring the radiographic image from a scanned film.

4. The method of claim 1 wherein processing the image comprises applying a difference-of-gradient filtering using Gaussian filters.

5. The method of claim 1 wherein the at least one feature indicative of image content comprise connectedness between pixels.

6. The method of claim 1 wherein one or more of the tile positions overlap each other.

7. The method of claim 1 further comprising displaying the acquired radiographic image and the corrected image simultaneously on a display.

8. The method of claim 1 further comprising applying an edge mask along an outer border of the image.

9. A method for correcting image speckle in a radiographic image, comprising:

acquiring a radiographic image from a scanned computed radiography medium;

processing the acquired image using a difference-of-gradient filtering to obtain a gradient image;

generating, from the gradient image, an initial set of pixels exhibiting speckle, wherein generating the initial set of pixels exhibiting speckle comprises evaluating image data values from the gradient image using a plurality of tiles, wherein each tile defines a partial portion of the image;

removing one or more pixels from the initial set of pixels according to a pixel connectedness metric and forming a mapping of pixels for replacement from the remaining set of pixels;

calculating a replacement pixel value for one or more pixels in the mapping;

replacing pixel values from the acquired radiographic image according to the calculated replacement pixels value to form a corrected image; and displaying, storing, or transmitting the corrected image.

10. The method of claim 9 further comprising applying pixel dilation before applying the pixel connectedness metric.

11. An imaging apparatus for correcting image speckle in a radiographic image, comprising:

an X-ray source energizable to direct radiation toward a subject;

a detector in the path of the X-ray radiation and disposed to record image content according to absorption by the subject;

a scanner energizable to form an image by scanning the detector;

a processor in signal communication with the scanner for acquiring the image, wherein the processor is programmed with stored instructions for: (a) processing the acquired image using a difference-of-gradient filtering to obtain a gradient image; (b) generating, from the gradient image, an initial set of pixels exhibiting speckle by evaluating image data values from the gradient image using a plurality of tiles, wherein each tile defines a partial portion of the image; (c) removing one or more pixels from the initial set of pixels according to a pixel connectedness metric and forming a mapping of pixels for replacement from the remaining set of pixels; (d) calculating a replacement pixel value for one or more pixels in the mapping; and (e) replacing pixel values from the acquired radiographic image according to the calculated replacement pixels value to form a corrected image; and a display for displaying the corrected image.

12. The method of claim 1 wherein processing the radiographic image to obtain a gradient image comprises generating a filtered image that accentuates image speckle artifacts in the image according to a gradient characteristic.

13. The method of claim 1 wherein generating an initial set of pixels exhibiting speckle comprises detecting an initial candidate set of speckle regions.

* * * * *